(12) United States Patent
Eaton et al.

(10) Patent No.: US 10,729,532 B2
(45) Date of Patent: Aug. 4, 2020

(54) BIFURCATED PROSTHESIS WITH AN INTERNAL LIMB

(71) Applicant: Cook Medical Technologies LLC, Bloomington, IN (US)

(72) Inventors: Elizabeth A. Eaton, Bloomington, IN (US); Blayne A. Roeder, Bloomington, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 128 days.

(21) Appl. No.: 15/886,061

(22) Filed: Feb. 1, 2018

(65) Prior Publication Data

US 2018/0228593 A1 Aug. 16, 2018

Related U.S. Application Data

(60) Provisional application No. 62/458,778, filed on Feb. 14, 2017.

(51) Int. Cl.
*A61F 2/07* (2013.01)
*A61F 2/06* (2013.01)
(Continued)

(52) U.S. Cl.
CPC .......... *A61F 2/07* (2013.01); *A61F 2/89* (2013.01); *A61F 2002/061* (2013.01);
(Continued)

(58) Field of Classification Search
CPC ........ A61F 2/07; A61F 2/89; A61F 2002/016; A61F 2002/067; A61F 2002/826;
(Continued)

(56) References Cited

U.S. PATENT DOCUMENTS 6,395,018 B1 5/2002 Castaneda
6,524,335 B1 2/2003 Hartley et al.
(Continued)

FOREIGN PATENT DOCUMENTS

WO WO 2006/034276 A1 3/2006
WO WO 2011/100290 A1 8/2011
(Continued)

OTHER PUBLICATIONS

Saari, P. et al., "*Fenestration of Aortic Stent Grafts—in Vitro Tests Using Various Device Combinations,*" Journal of Vascular and Interventional Radiology, vol. 22, Issue 1, (2011), pp. 89-94—Abstract Only—pp. 1-2.
(Continued)

*Primary Examiner* — Christopher D. Prone
*Assistant Examiner* — Tiffany P Shipmon
(74) *Attorney, Agent, or Firm* — Brinks Gilson & Lione (57) ABSTRACT

A bifurcated endovascular prosthesis that includes a tubular main body having a diameter, a proximal end, a distal end, an internal lumen extending from the proximal end to the distal end, an anterior side, and a posterior side. The anterior and posterior sides are opposite each other circumferentially around the internal lumen. The prosthesis also includes a first limb that extends from the distal end of the tubular main body along the anterior side of the main body. The first limb has a diameter less than the diameter of the tubular main body and having a proximal end and a distal end. The prosthesis also includes a fenestration adjacent to the proximal end of the first limb. The fenestration extends from the proximal end of the first limb to the posterior side of the tubular main body. The prosthesis also includes a second limb that extends within the internal lumen from the fenestration toward the proximal end of the tubular main body. The fenestration has a substantially diamond shape and a nonlinear profile, and the second limb extends into the lumen along the posterior side of the tubular main body.

21 Claims, 6 Drawing Sheets

(51) Int. Cl.
*A61F 2/82* (2013.01)
*A61F 2/89* (2013.01)

(52) U.S. Cl.
CPC ... *A61F 2002/067* (2013.01); *A61F 2002/826* (2013.01); *A61F 2220/0075* (2013.01); *A61F 2230/0019* (2013.01); *A61F 2240/001* (2013.01)

(58) Field of Classification Search
CPC ...... A61F 2220/0075; A61F 2230/0019; A61F 2240/001
See application file for complete search history.

(56) References Cited

U.S. PATENT DOCUMENTS

| | | |
|---|---|---|
| 6,949,121 B1 | 9/2005 | Laguna |
| 7,014,653 B2 | 3/2006 | Ouriel et al. |
| 7,407,509 B2 | 8/2008 | Greenberg et al. |
| 7,955,374 B2 | 6/2011 | Erickson et al. |
| 7,963,960 B2 | 6/2011 | Bruszewski et al. |
| 8,100,960 B2 | 1/2012 | Bruszewski |
| 8,241,349 B2 | 8/2012 | Davidson et al. |
| 8,915,956 B2 | 12/2014 | Schaeffer et al. |
| 2006/0095118 A1 | 5/2006 | Hartley |
| 2009/0043377 A1 | 2/2009 | Greenberg et al. |
| 2009/0125097 A1 | 5/2009 | Bruszewski et al. |
| 2009/0228020 A1 | 9/2009 | Wallace et al. |
| 2009/0259290 A1 | 10/2009 | Bruszewski et al. |
| 2009/0264988 A1 | 10/2009 | Mafi et al. |
| 2012/0041544 A1 | 2/2012 | Wolf |
| 2012/0046657 A1 | 2/2012 | Biadillah et al. |
| 2012/0239132 A1 | 9/2012 | Naor et al. |
| 2013/0289702 A1 | 10/2013 | Coghlan et al. |
| 2013/0296998 A1 | 11/2013 | Leotta et al. |
| 2015/0057737 A1 | 2/2015 | Ondersma et al. |
| 2015/0119975 A1 | 4/2015 | Mastracci |
| 2016/0106564 A1 | 4/2016 | Roeder et al. |

FOREIGN PATENT DOCUMENTS

| | | |
|---|---|---|
| WO | WO 2015/040413 A2 | 3/2015 |
| WO | WO 2015/061669 A1 | 4/2015 |
| WO | WO-2015061669 A1 * | 4/2015 |
| WO | WO 2015/063780 A2 | 5/2015 |

OTHER PUBLICATIONS

Stephen, E. et al., "*A Novel Cautery Instrument for On-Site Fenestration of Aortic Stent-Grafts: A Feasibility Study of 18 Patients,*" Journal of Endovascular Therapy, 20, (2013) pp. 638-646.

European Extended Search Report and Written Opinion for European Application No. 18275017.4 dated May 29, 2018 (7 pages).

* cited by examiner

BIFURCATED PROSTHESIS WITH AN INTERNAL LIMB

RELATED APPLICATIONS

The present patent document claims priority to and the benefit of the filing date under 35 U.S.C. § 119(e) to U.S. Provisional Patent Application Ser. No. 62/458,778, which was filed on Feb. 14, 2017, and is hereby incorporated by reference in its entirety.

BACKGROUND

1. Technical Field

The present invention relates to prostheses having an internal limb, such as for abdominal aortic stent grafts, for repair of an existing prosthesis and methods of cannulating the contralateral gate of a prosthesis through an existing stent graft leg or limb.

2. Background Information

Endovascular aortic aneurysm repair is practiced by a wide range of physicians across varying specialties. An aortic aneurysm is an enlargement of the aorta of a patient caused by weakening in the wall of the aorta. If an aortic aneurysm is untreated, it may rupture and cause serious health complications.

The surgical procedure for endovascular aortic aneurysm repair involves the placement of a stent graft within the aorta of a patient to seal off the aneurysm from blood flow to prevent the aneurysm from expanding. Physicians often use the procedure to treat abdominal aortic aneurysms (AAA) and also to treat thoracic aortic aneurysms (TAA) and aneurysms in other locations of the patient. One type of abdominal aortic aneurysm is an infra-renal abdominal aortic aneurysm, which is located in the abdominal aorta below the renal arteries.

As demographics continue to expand and graft recipients live longer, there is an increase in the prevalence and complexity of repair cases. The patient's anatomy may change over time and lead to a size mismatch of the original stent graft within the patient's anatomy or may result in movement of the stent graft within the patient's anatomy. The disease may also progress beyond the previously repaired area, which may result in endoleak at the stent graft seal zone or movement (migration) of the stent graft within the patient's anatomy. Additionally and/or alternatively, the original stent graft may have been implanted in suboptimal anatomy or the design or construction of the stent graft proves insufficient over time. These instances also may result in leaking of the stent graft, movement of the stent graft within the patient's anatomy, or other complications.

In addition, as the patient ages, other factors may also dictate treatment of the aortic aneurysm, including the frequency and severity of a patient's comorbidities and an increase in the patient's general surgical risk. These factors may rule the patients out as candidates for explant of the original stent graft during open repair.

To re-intervene endovascularly, the physician contends with not only maneuvering through the patient's anatomy, that potentially has grown more challenging or hostile in the interim, but also the body, legs, and limbs of the original stent graft. To reline the original stent graft, the physician must identify a landing zone for a new stent graft proximal to the original stent graft. This can mean new or further involvement of some of the visceral arteries, such as the renal arteries, the superior mesenteric artery, and the celiac artery. In most cases, the ostia of these vessels must be maintained; this frequently involves stenting with a covered stent through fenestrations in the new stent graft or apposing a scallop fenestration in the graft to the aortic wall at the level of the ostium. Another factor is the design of the original stent graft: the distance between the renal arteries and the proximal edge of the original stent graft affects whether the visceral arteries will be involved; and the distance between the proximal edge of the original stent graft and the bifurcation of the original stent graft dictates what kind of device will fit inside the existing environment. Some devices have a graft bifurcation located much farther proximally from the native aortic bifurcation than others, which truncates the acceptable body length of any device used in a reintervention. These factors create a highly complex procedure.

BRIEF SUMMARY

This invention concerns a bifurcated prosthesis having an internal limb that provides easy access for cannulating the contralateral gate of a prosthesis through an existing stent graft leg or limb and methods of cannulating the contralateral gate of a prosthesis through an existing stent graft leg or limb.

A bifurcated endovascular prosthesis that includes a tubular main body having a diameter, a proximal end, a distal end, an internal lumen extending from the proximal end to the distal end, an anterior side, and a posterior side. The anterior and posterior sides are opposite each other circumferentially around the internal lumen. The prosthesis also includes a first limb that extends from the distal end of the tubular main body along the anterior side of the main body. The first limb has a diameter less than the diameter of the tubular main body and having a proximal end and a distal end. The prosthesis also includes a fenestration adjacent to the proximal end of the first limb. The fenestration extends from the proximal end of the first limb to the posterior side of the tubular main body. The prosthesis also includes a second limb that extends within the internal lumen from the fenestration toward the proximal end of the tubular main body. The fenestration has a substantially diamond shape and a nonlinear profile, and the second limb extends into the lumen along the posterior side of the tubular main body.

A bifurcated endovascular prosthesis including a tubular main body that has a diameter, a proximal end, a distal end, an internal lumen extending from the proximal end to the distal end, an anterior side, and a posterior side. The anterior and posterior sides are opposite each other circumferentially around the internal lumen. The prosthesis also includes a first limb that extends from the distal end of the tubular main body along the anterior side of the main body and is circumferentially centered on the anterior side of the main body. The first limb has a tubular body, a proximal end and a distal end. The prosthesis also includes a fenestration that is adjacent to the proximal end of the first limb. The fenestration extends from the proximal end of the first limb to the posterior side of the tubular main body. The prosthesis also includes a second limb that extends within the internal lumen from the fenestration toward the proximal end of the tubular main body. The fenestration has a substantially diamond shape and a nonlinear profile, and the second limb extends into the lumen along the posterior side of the tubular main body and is circumferentially centered on the posterior side of the tubular main body.

A method of cannulating a contralateral gate of a bifurcated prosthesis that includes inserting the bifurcated prosthesis into an existing bifurcated prosthesis. The existing bifurcated prosthesis includes a tubular main body having a diameter, a proximal end, a distal end, an internal lumen extending from the proximal end to the distal end, an anterior side, and a posterior side. The anterior and posterior sides being opposite each other circumferentially around the internal lumen. The existing bifurcated prosthesis also includes a first limb that extends from the distal end of the tubular main body and is circumferentially centered between the anterior and posterior sides. The existing bifurcated prosthesis also includes a second limb extending from the distal end of the tubular main body and is circumferentially centered between the anterior and posterior sides. The first and second limbs are positioned opposite to each other circumferentially around the internal lumen of the existing bifurcated prosthesis. The bifurcated prosthesis includes a tubular main body having a diameter, a proximal end, a distal end, an internal lumen extending from the proximal end to the distal end, an anterior side, and a posterior side. The anterior and posterior sides being opposite each other circumferentially around the internal lumen. The bifurcated prosthesis also includes a first limb that extends from the distal end of the tubular main body along the anterior side of the main body and is circumferentially centered on the anterior side of the main body. The first limb has a tubular body, a proximal end and a distal end. The bifurcated prosthesis also includes a fenestration that is adjacent to the proximal end of the first limb. The fenestration extends from the proximal end of the first limb to the posterior side of the tubular main body. The bifurcated prosthesis also includes a second limb that extends within the internal lumen from the fenestration toward the proximal end of the tubular main body. The fenestration has a substantially diamond shape and a nonlinear profile, and the second limb extends into the lumen along the posterior side of the tubular main body and is circumferentially centered on the posterior side of the tubular main body. When inserting the bifurcated prosthesis into the existing bifurcated prosthesis, the tubular main body of the bifurcated prosthesis is inserted into the tubular main body of the existing bifurcated prosthesis, the first limb of the bifurcated prosthesis is inserted into the first limb of the existing bifurcated prosthesis, and the fenestration of the bifurcated prosthesis is positioned over the second limb of the existing bifurcated prosthesis. The method also includes inserting a limb extension having a tubular body, a proximal end, and a distal end, into the second limb of the existing bifurcated prosthesis through the fenestration of the bifurcated prosthesis and through the second limb of the bifurcated prosthesis.

The accompany drawings, which are incorporated herein and constitute part of this specification, and, together with the general description given above and the detailed description given below, serve to explain features of the present invention.

DETAILED DESCRIPTION OF THE DRAWINGS AND THE PRESENTLY PREFERRED EMBODIMENTS

In the present disclosure, the term "proximal" refers to a direction that is generally closest to the heart during a medical procedure, while the term "distal" refers to a direction that is farthest from the heart during a medical procedure.

The term "fenestration" refers to an opening provided through a surface of a prosthesis from the interior of the prosthesis to the exterior of the prosthesis. A fenestration may have any one of a variety of geometries including circular, semi-circular, oval, oblong, diamond, or other geometries.

The term "prosthesis" refers to any device for insertion or implantation into or replacement for a body part or a function of that body part. The term also may refer to a device that enhances or adds functionality to a physiological system. The term prosthesis may include, for example and without limitation, a stent, stent-graft, filter, valve, balloon, embolization coil, and the like.

Figures 1, 2, 3:
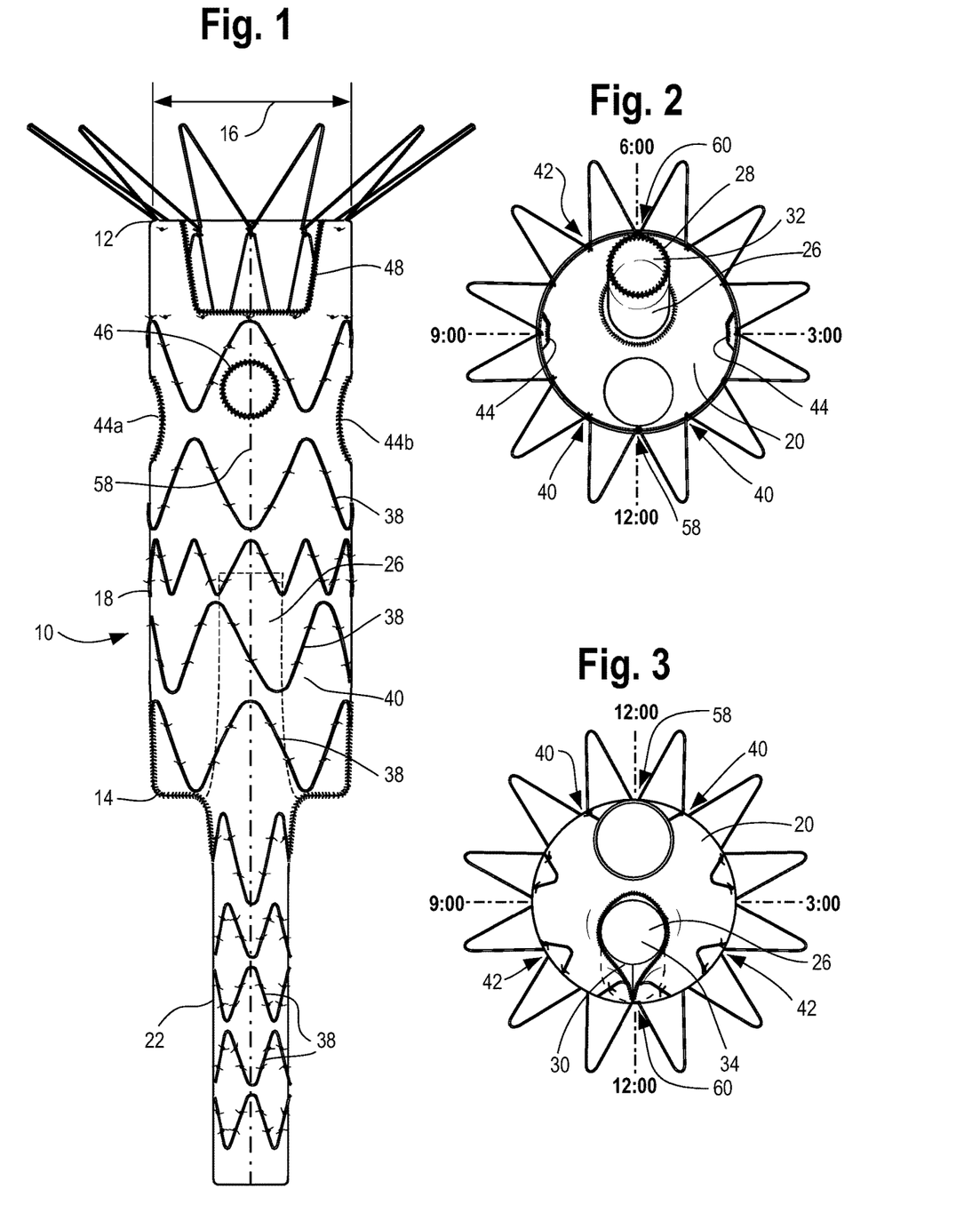
FIG. 1 shows a front view of a bifurcated prosthesis with an internal limb.
FIG. 2 shows a top view of the bifurcated prosthesis of FIG. 1.
FIG. 3 shows a bottom view of the bifurcated prosthesis of FIG. 1.
Figure 4:
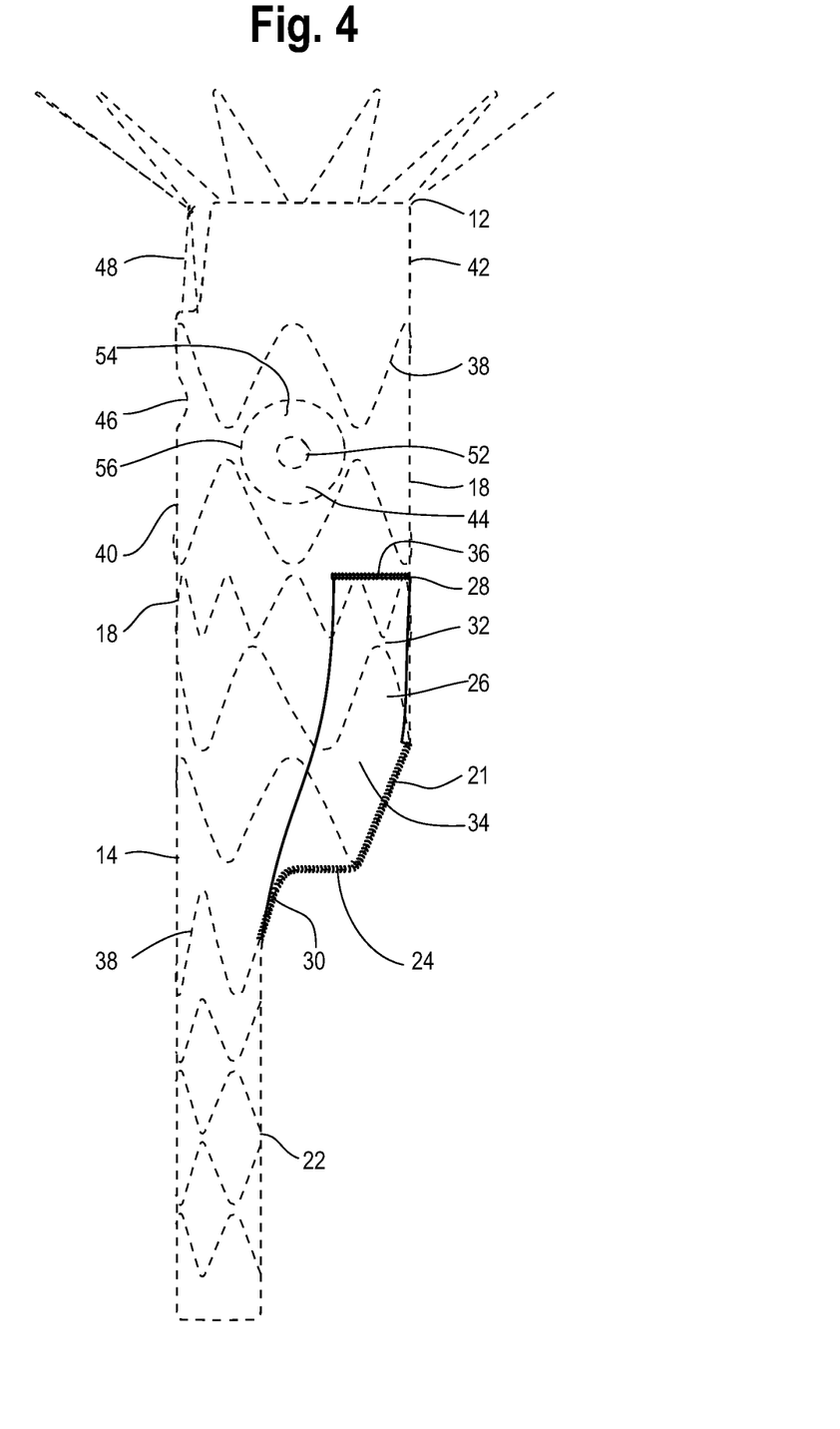
FIG. 4 shows a side view of the bifurcated prosthesis of FIG. 1.
Figure 5:
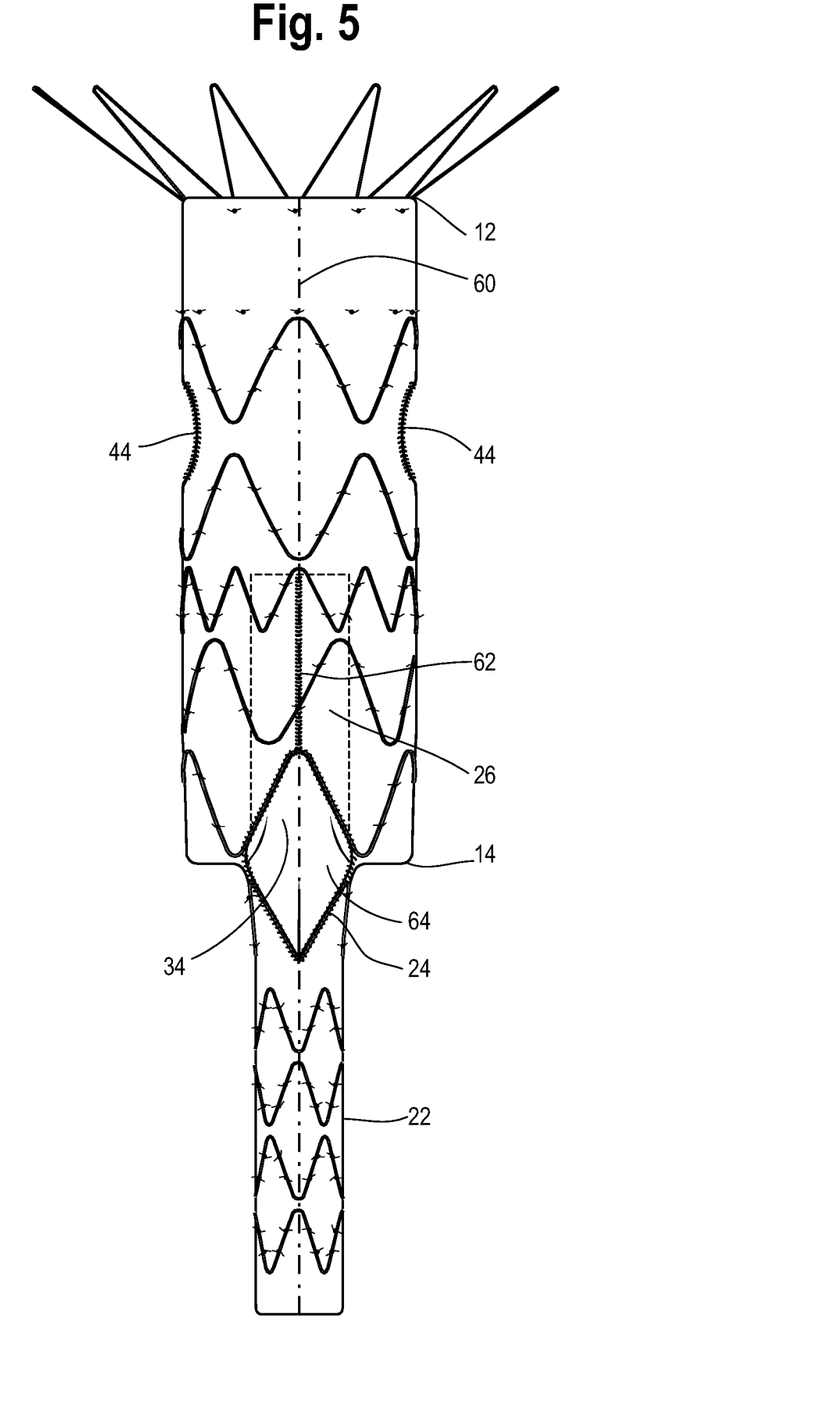
FIG. 5 shows a rear view of the bifurcated prosthesis of FIG. 1.

FIG. 1 shows a front view of a prosthesis 10. The prosthesis 10 may include a bifurcated stent graft including a proximal end 12, a distal end 14, a diameter 16, a tubular main body 18 that extends from the proximal end 12 to the distal end 14, and an internal lumen 20. The prosthesis 10 also includes one external distal leg 22 or a first limb that extends distally from the distal end 14 of the prosthesis 10. The prosthesis 10 also includes a frustoconical midsection 21 adjacent to and on a side opposite to the external distal leg 22 and a fenestration 24 that is located in the frustoconical midsection 21, as shown in FIGS. 4-5. Some bifurcated stent grafts may include two external distal legs; however, the bifurcated stent graft in the present disclosure includes one external distal leg 22 and the fenestration 24. The external distal leg 22 can be sized and dimensioned for insertion into an iliac artery or existing stent graft limb/leg/body.

The fenestration 24 includes a diamond shaped fenestration, as shown in FIG. 5. In other examples, the fenestration 24 of the prosthesis 10 may include circular, semi-circular, oval, oblong, or other geometries, and the diamond shape may include a geometry of a diamond, rhombus or parallelogram shape with oblique angles or non-oblique angles, sides with equal or varying lengths, or approximate geometries or the same, e.g. a diamond shape with rounded corners or a diamond shape that may include minor sides in addition to the four main sides, and such examples are within the scope of this disclosure.

The internal limb 26 extends from the fenestration 24 and into the internal lumen 20 of the tubular main body 18 toward the proximal end 12 of the prosthesis 10. The internal limb 26 comprises a proximal end 28, a distal end 30, a tubular body 32 that extends from the proximal end 28 to the distal end 30, and an internal lumen 34. The internal limb is made of a graft material that may include a flexible material, such as polytetrafluoroethylene (PTFE) or expanded PTFE (ePTFE), a polyester material, or other materials that allow for a seal with the prosthesis 10. The material allows an internal limb 26 to be easily expanded and collapsed.

The internal limb 26 may also include a ring 36 positioned at the proximal end 28 of the internal limb 26. The ring 36 maintains the patency of the internal lumen 34 of the internal limb 26 and provides structure to the internal limb 26. The ring 36 also allows for something to seal against, while also minimizing packing density because it will collapse during loading of the internal limb 26. The material of the ring 36 may include nitinol or other shape memory or elastic metal. As shown in FIG. 2, the ring 36 may be sewn or stitched to the proximal end 28 of the internal limb 26. The ring 36 may have a pure circular or other shape, which may aid in support, packing, and/or collapse.

The prosthesis 10 and the internal limb 26 may include a plurality of stents 38, such as the Z-stent or Gianturco stent design, or be free of stents. As shown in FIG. 1, the prosthesis 10 includes the plurality of stents 38 that are Z-stents. However, in other examples, the prosthesis 10 may be free of the stents 38. Also, as shown in FIG. 2, the internal limb 26 may be free of stents 38. Although the internal limb 26 is described as free of any stents, the disclosure is not so limited. In other examples, the internal limb 26 may include a stent pattern such as the Z-stent or Gianturco stent design, and such examples are within the scope of this disclosure. Each Z-stent may include a series of substantially straight segments or struts interconnected by a series of bent segments or bends. The bent segments may include acute bends or apices. The Z-stents are arranged in a ZigZag configuration in which the straight segments are set at angles relative to one another and are connected by the bent segments. This design provides both significant radial force as well as longitudinal support. In tortuous anatomy, branches, or fenestrations, it may be preferable to use alternative stents or modifications to the Z-stent design to avoid stent-to-stent contact. Alternative stents may include, for example, annular or helical stents. Furthermore, in complex anatomical situations, external stents may have the potential to become intertwined with the wires or other devices utilized to ensure branch vessel access, sealing, and fixation. Thus, in some instances, it may be desirable to affix some of the stents 38 to the external and/or internal surfaces of the internal limb 26.

The tubular main body 18 of the prosthesis 10 includes an anterior side 40 and a posterior side 42. The anterior and posterior sides 40, 42 are opposite to each other circumferentially around the internal lumen 20. The anterior side 40 may extend circumferentially around approximately half of the circumference of the tubular main body 18. The posterior side 42 may extend circumferentially around approximately the other half of the circumference of the tubular main body 18. The posterior side 42 of the tubular main body 18 may be positioned opposite the anterior side 40 with respect to the circumference of the tubular main body 18. In other words, a plane may be defined to include the longitudinal axis of the tubular main body 18. The anterior side 40 may be positioned on one side of the plane, and the posterior side 42 may be positioned on the opposite side of the plan from the anterior side 40. The anterior side 40 and the posterior side 42 may cooperatively form the tubular main body 18.

Figure 7:
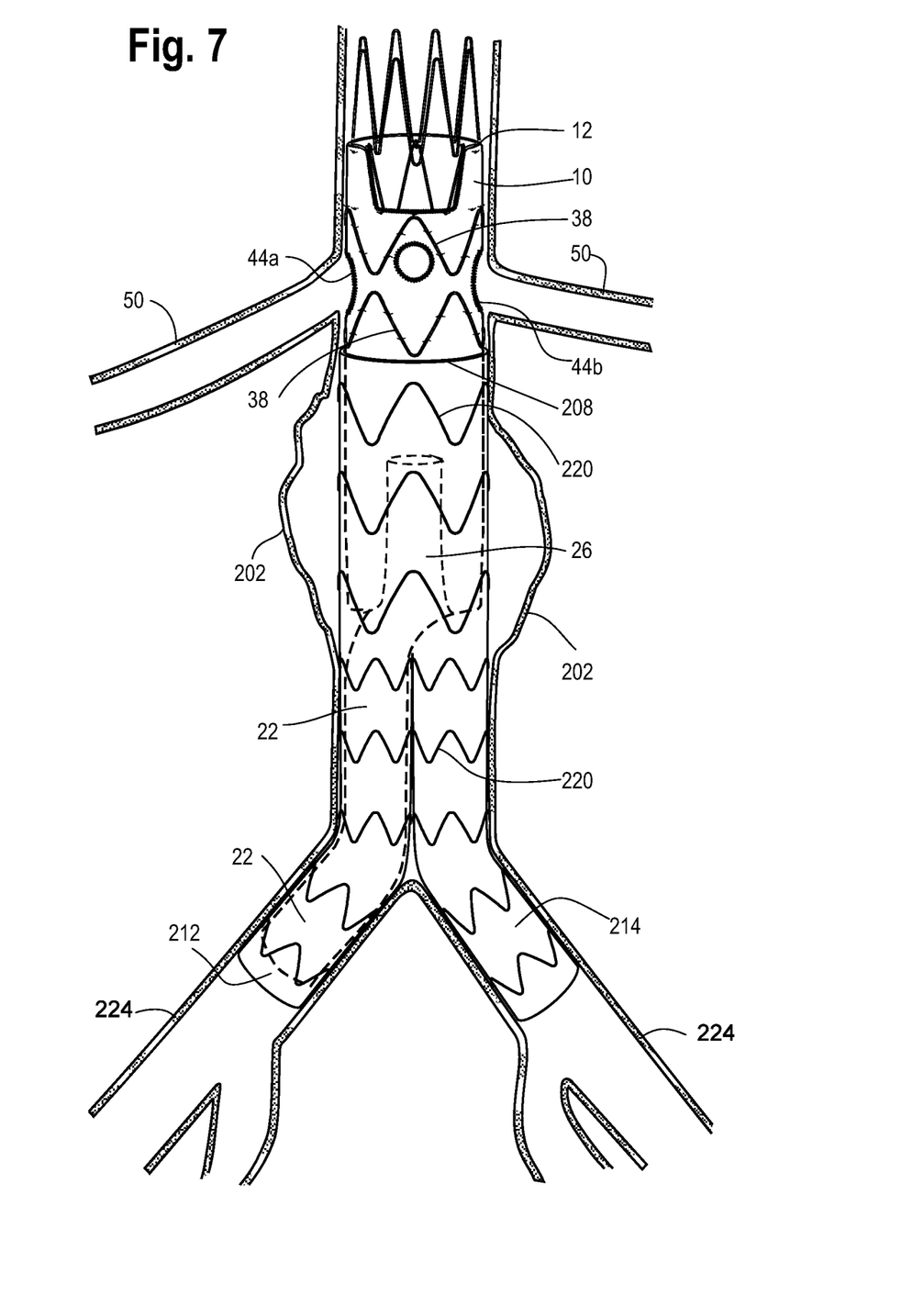
FIG. 7 shows a perspective view of the bifurcated prosthesis of FIG. 1 inserted within the existing prosthesis of FIG. 6 inside the patient's body.
Figure 8:
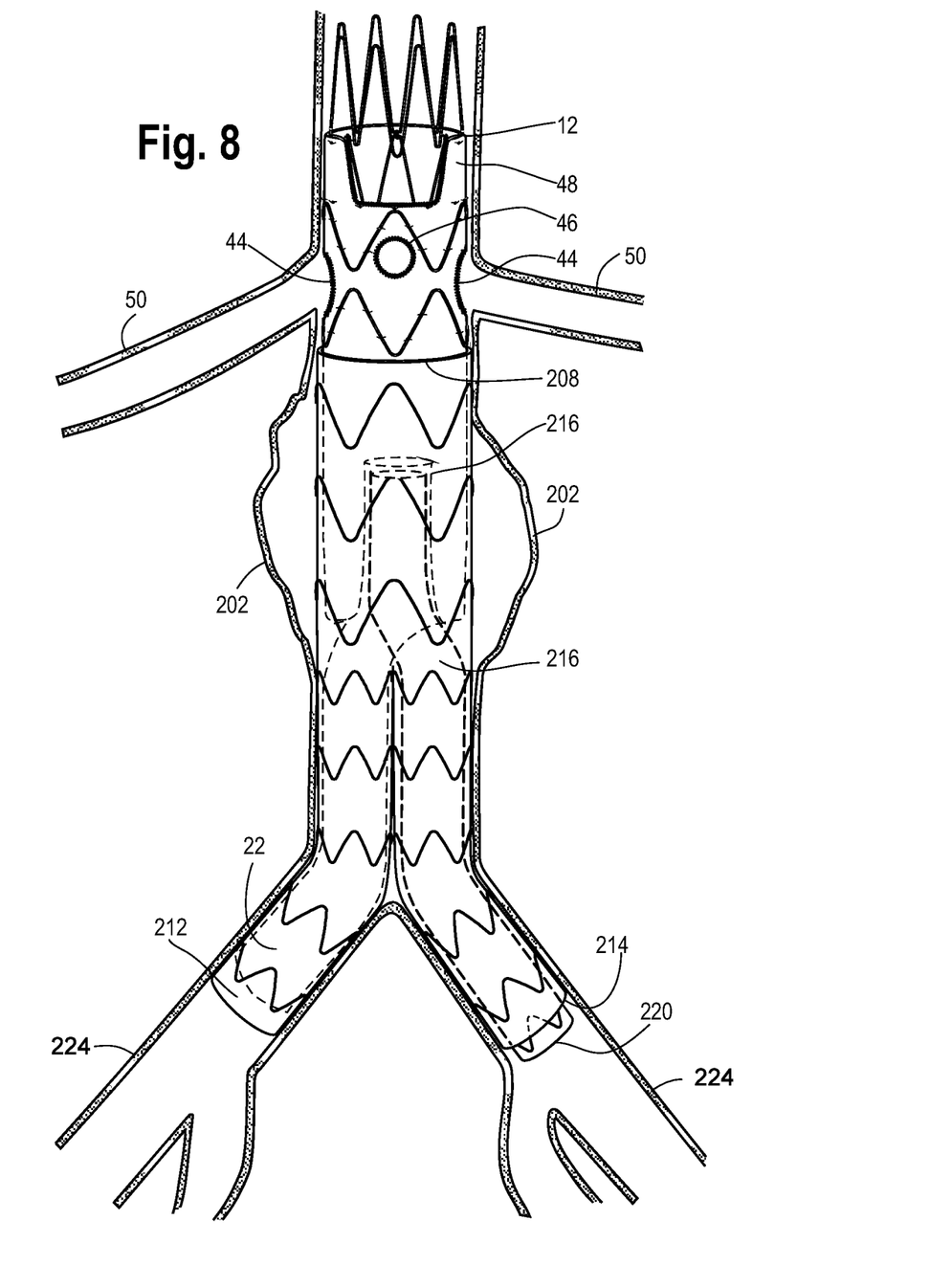
FIG. 8 shows a perspective view of an iliac limb extension inserted into the bifurcated prosthesis of FIG. 1 and the existing prosthesis of FIG. 6 inside the patient's body.

The tubular main body 18 may include a plurality of fenestrations in addition to fenestration 24. The plurality of fenestrations may be pivotable or non-pivotable. The tubular main body 18 may include two pivotable fenestrations 44, a non-pivotable fenestration 46, and a scallop 48 as shown in FIGS. 1-2, 4-5, and 7-8. Although the tubular main body 18 is described as including two pivotable fenestrations 33 and a non-pivotable fenestration 46, the disclosure is not so limited. In other examples, any of the fenestrations may be pivotable or non-pivotable, and such examples are within the scope of this disclosure. The pivotable fenestrations 445 may be positioned on the tubular main body 18 to radially align with, for example, the renal arteries 50, as shown in FIGS. 7-8. The non-pivotable fenestration 46 may be positioned on the tubular main body 18 to radially align with, for example, the superior mesenteric artery (SMA). The scallop 48 may be configured to align with the celiac artery. It will be recognized by one of ordinary skill in the art that the prosthesis 10 may include any number of openings or fenestrations of any type. Also, the fenestrations may be arranged on the prosthesis 10 in any manner. Preferably, the fenestrations may be arranged to correspond to a particular position within the anatomy into which the prosthesis 10 is intended to be placed.

The pivotable fenestrations 44 may include an inner perimeter 52 surrounding the fenestration 44, a band 54 surrounding the inner perimeter 52, and an outer perimeter 56 surrounding the band 54, as shown in FIG. 4. The outer perimeter 56 may have a diameter that is greater than a diameter of the inner perimeter 52. The inner perimeter 52, the band 54, and the outer perimeter 56 may be substantially concentric with one another if brought into the same plane, for example, the surface plane of the graft. The inner perimeter 52, the band 54, and the outer perimeter 56 may form an extension having a hemispherical shape, resembling a dome, or a frustoconical cone extending from the surface of the tubular main body 18. The pivotable fenestration 44 may be positioned at the peak or top of the extension. The pivotable fenestration 44 may be placed in a concave orientation or a convex orientation. In the concave orientation, the extension may extend into the internal lumen 20 of the tubular main body 18, as shown in FIG. 2. In the convex orientation, the extension may extend away from the internal lumen 20. The pivotable fenestration 44 may be movable between the concave orientation and the convex orientation. The pivotable fenestration 44 also may be placed in any position between the concave orientation and the convex orientation. For example, the band 54 may be folded, bent, gathered, pleated, or otherwise manipulated such that the fenestration 44 is generally aligned with the surface plane of the tubular main body 18.

The outer perimeter 56 of the pivotable fenestration 44 may be affixed to the tubular main body 18 by any attachment method including suturing circumferentially about an aperture disposed through the tubular main body 18. The band 54 may be sufficiently flexible to permit the fenestration 44 to move such that a branch prosthesis disposed in the fenestration 44 may be oriented upwardly, downwardly, laterally, diagonally, and the like relative to the surface of the tubular main body 18. In some examples, the band 54 may permit the fenestration 44 to move up to about 180 degrees relative to the surface plane of the tubular main body 18. Accordingly, the pivotable fenestration 44 may allow the prosthesis 10 to be used in a variety of patients due to its ability to adapt to the variance in the positioning of the diseased branch vessels. For example, if a branch vessel is or becomes offset longitudinally or axially from a pivotable fenestration 44, the pivotable fenestration 44 may pivot the prosthesis 10 in the necessary direction and to the necessary degree to maintain the prosthesis 10 in place in the branch vessel.

An important aspect of the fenestrations 44, 46 and the scallop 48 on the prosthesis 10 is to maintain blood flow to the visceral vessels, including the renal arteries 50, the superior mesenteric artery, and the celiac artery, after implantation of the prosthesis 10 within the abdominal aorta. In some instances, the fenestrations 44, 46 are used to allow a prosthesis, stent, wire and other device to access the visceral vessels. When the internal limb 26 is inserted through the fenestration 24 and into the internal lumen 20 of the tubular main body 18, the internal limb 26 occupies a portion of the internal lumen 20. Therefore, positioning the internal limb 26 within the internal lumen 20 to avoid the fenestrations 44, 46 may minimize interference within the internal lumen 20 of the tubular main body 18.

For example, the prosthesis 10 may be configured to extend between a point proximal to the renal arteries 50 and a point distal to the renal arteries 50. Thus, the scallop 48 may be configured to align with the celiac artery, the pivotable fenestrations 44 may be configured to align with the renal arteries 50, and the non-pivotable fenestration 46 may be configured to align with the superior mesenteric artery. As previously described, although the tubular main body 18 is described as including two pivotable fenestrations 44 and a non-pivotable fenestration 46, the disclosure is not so limited. In other examples, any of the fenestrations may be pivotable or non-pivotable, and such examples are within the scope of this disclosure. The scallop 48 may be positioned circumferentially on an anterior point 58 of the tubular main body 18 and longitudinally at the proximal end 12 of the tubular main body 18. The anterior point 58 may extend generally longitudinally along the tubular main body 18 and may be substantially circumferentially centered on the anterior side 40 of the tubular main body 18, as shown in FIG. 1. The tubular main body 18 also includes a posterior point 60 that is substantially circumferentially centered on the posterior side 42 of the tubular main body 18, as shown in FIG. 5.

The non-pivotable fenestration 46 may be positioned circumferentially on the anterior point 58 of the tubular main body 18 and longitudinally distal to the scallop 48. The pivotable fenestrations 44 may be spaced from one another by a predetermined distance around the circumference of the tubular main body 19. For example, the first pivotable fenestration 44a may be configured to align with the right renal artery 50 and may be spaced a first circumferential distance from the anterior point 58 of the tubular main body 18. The second pivotable fenestration 44b may be configured to align with the left renal artery 50 and may be spaced a second circumferential distance from the anterior point 58 of the tubular main body 18. The first and second circumferential distances may be of substantially equal lengths in opposite directions relative to the anterior point 58 of the tubular main body 18. Alternatively, the first and second circumferential distances may be different from one another, for example, to correspond to the anatomy of a particular patient or patients. The first and second pivotable fenestrations 44a, 44b may be positioned at substantially the same longitudinal position along the tubular main body 76. Alternatively, the first and second pivotable fenestrations 85a, 85b may be offset longitudinally with respect to one another, for example, to correspond to the anatomy of a particular patient or patients. The first and second pivotable fenestrations 44a, 44b may be positioned longitudinally distal to the non-pivotable fenestration 46 and the scallop 48, as shown in FIG. 4. As shown in FIGS. 1-2, the pivotable fenestrations 44 may be positioned circumferentially centered between the anterior and posterior sides 40, 42. In other examples, the pivotable fenestrations 44 may be both positioned on the anterior side 40 or the posterior side 42.

The external distal leg 22 and the fenestration 24 are spaced apart from one another by a predetermined distance around the circumference of the prosthesis 10. Specifically, the distal leg 22 is positioned longitudinally distal to the non-pivotal fenestration 46 and spaced a circumferential distance from the anterior point 58 of the tubular main body 18. The fenestration 24 is also positioned longitudinally distal to the non-pivotal fenestration 46 and spaced a circumferential distance from the anterior point 58 of the tubular main body 18. The circumferential distance of the distal leg 22 and the fenestration 24 from the anterior point 58 is approximately equal. Thus, the distal leg 22 and the fenestration 24 may be positioned on the prosthesis 10 approximately 90 degrees from the anterior point 58 of the tubular main body 18 with respect to the circumference of the prosthesis 10 in opposite directions, or in other words, the distal leg 22 and the fenestration 24 may be positioned on opposite sides of the prosthesis 10 relative to the anterior point 58. For example, the distal leg 22 and the fenestration 24 may be circumferentially centered between the anterior and posterior sides 40, 42 of the tubular main body 18 and 180 degrees from one another with respect to the circumference of the tubular main body 18 as shown in FIGS. 1-3.

As shown in FIGS. 2-4, when the internal limb 26 extends from the fenestration 24 into the internal lumen 20 toward the proximal end 12 of the prosthesis 10 and along the posterior side 42 of the tubular main body 18. In other words, the internal limb 26 extends vertically through the internal limb 26 and along the posterior side 42 of the tubular main body 18 such that the internal limb 26 is positioned in the internal lumen 20 along the posterior point 60 to avoid the pivotable fenestrations 44 and non-pivotable fenestration 46.

The internal limb 26 may be sewn, sutured or stitched 62 to the stent graft body of the tubular main body 18 to maintain the positioning of the internal limb 26 within the prosthesis 10, as shown in FIG. 5. The internal limb 26 is only sewn, sutured, or stitched 62 along the side of its tubular wall that is in contact with the tubular main body 18 to ensure the internal limb 26 maintains its position and (if desired) patency within the internal lumen 20. For example, as shown in FIG. 5, the internal limb 26 may be sewn, sutured, or stitched 62 along the posterior side 42 and posterior point 60 of the prosthesis 10.

The fenestration 24 with the internal limb 26 connected to the fenestration 24 may not take its shape naturally. Thus, the internal limb 26 creates a shelf-like configuration when attached to the fenestration 24 and opens the fenestration 24. For example, as shown in FIG. 4, the proximal half of the fenestration 24 may collapse distally and lies at an angle, such as 90 degrees or greater, to the distal half of the fenestration 24. This orientation or shelf-like configuration of the fenestration 24 creates an effectively larger target for an approaching wire, catheter, dilator or other device to be easily inserted through the fenestration 24 and facilitates cannulation.

As shown in FIG. 5, the internal limb 26 also creates a smooth seamless slope or path 64 for an approaching wire, catheter, dilator or other device to be inserted through the fenestration 24 and slide unimpeded through the internal limb 26. As described previously, the smooth seamless slope 100 allows for ease of cannulation and minimizes the areas where an approaching wire, catheter, dilator or other device may catch or snag when moving through the internal limb 26.

The circumferential positions of the various components or features of the prosthesis 10 may be described with reference to a clock face as shown in FIGS. 2-3. For example, the clock face may be positioned such that 12 o'clock corresponds to the anterior point 58 of the prosthesis 10 and 6 o'clock corresponds to the posterior point 60 of the prosthesis 10, such as looking up from a patient's distal aorta. Thus, the non-pivotable fenestration 46 and/or the scallop 48 may be positioned circumferentially at approximately 12 o'clock, i.e., along the anterior point 58 of the prosthesis 10. The pivotable fenestrations 44 may be positioned circumferentially on the prosthesis 10 at 3 o'clock and 9 o'clock. In other examples, the pivotable fenestrations 44 may be positioned circumferentially between approximately 1:30 to 3:00 o'clock and between approximately 9:00 to 10:30 o'clock, respectively. Such positioning may vary to enable the pivotable fenestrations 44 to generally align with the renal arteries 50 as previously described. The external distal leg 22 may be positioned circumferentially at 12 o'clock and the fenestration 24 may be positioned circumferentially at 6 o'clock. The internal limb 26 may be positioned circumferentially at 6 o'clock such that the proximal end 28 of internal limb 26 is positioned circumferentially at 6 o'clock as shown in FIGS. 2-3. Thus, the orientation of the internal limb 26 to the clock position of 6 o'clock positions the internal limb 26 away from the fenestrations 44, 46 and the scallop 48 to minimize interference within the prosthesis 10.

The prosthesis 10 with the internal limb 26 may be inserted into an original or existing prosthesis 200 that needs repair. The internal limb 26 allows a wire, catheter, dilator or other device, such as an iliac limb extension, to be inserted through the original or existing stent graft leg or limb and the internal limb 26 and for cannulation of the contralateral gate of the prosthesis 10, or the side of the prosthesis 10 opposite the external distal leg 22 of the prosthesis 10, through the existing stent graft leg or limb.

Figure 6:
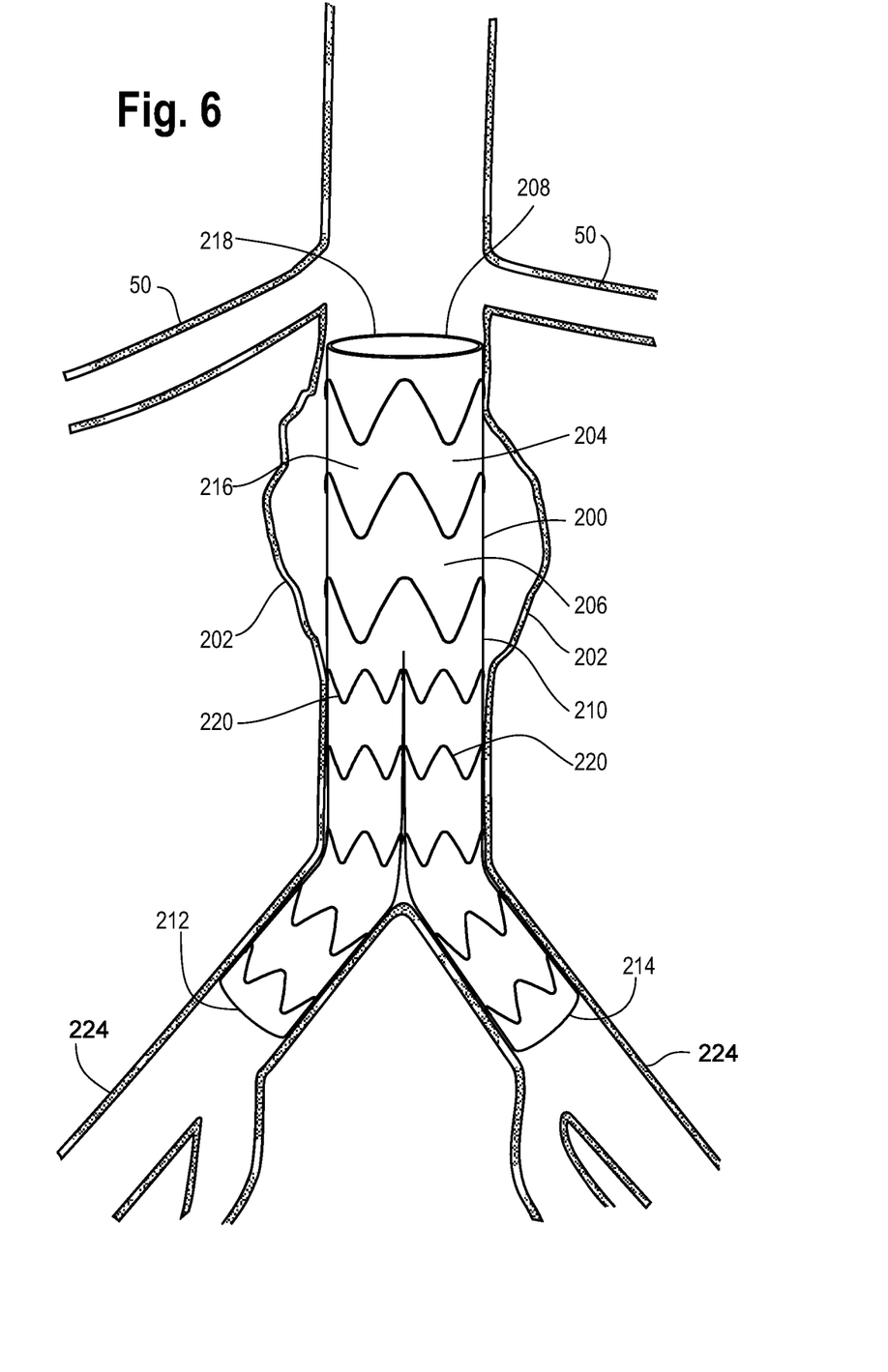
FIG. 6 shows a perspective view of an existing prosthesis inside a patient's body that needs repair.

FIGS. 6-8 show an example of an existing prosthesis 200 that is a bifurcated prosthesis inside a patient's body over an aneurysm 202. The existing prosthesis 200 includes a stent graft body 204 that includes a main tubular body 206 having a proximal end 208 and a distal end 210, a first limb 212 extending from the distal end 210 of the main tubular body 206, and a second limb 214 also extending from the distal end 210 of the main tubular body 206. The first limb 212 and the second limb 214 extend through the patient's iliac arteries 224. Although FIGS. 6-8 show the proximal end 208 of the main tubular body 206 of the existing prosthesis 200 positioned below the renal arteries 50, the existing prosthesis 200 may be positioned above or next to the renal arteries 50. In such an example, the existing prosthesis 200 may also include fenestrations within the stent graft body 204 to allow blood flow from the renal arteries 50. Similar to the prosthesis 10, the existing prosthesis 200 may include a plurality of stents, as described previously above, or be free of stents. In FIGS. 6-8, the existing prosthesis 200 includes a plurality of stents 222.

The main tubular body 206 of the existing prosthesis 200 includes an anterior side 216 and a posterior side 218. The anterior and posterior sides 216, 218 are opposite to each other circumferentially around the main tubular body 206. The anterior side 216 may extend circumferentially around approximately half of the circumference of the main tubular body 206. The posterior side 218 may extend circumferentially around approximately the other half of the circumference of the main tubular body 206. The posterior side 218 of the main tubular body 206 may be positioned opposite the anterior side 216 with respect to the circumference of the main tubular body 206. In other words, a plane may be defined to include the longitudinal axis of the main tubular body 206. The anterior side 216 may be positioned on one side of the plane, and the posterior side 218 may be positioned on the opposite side of the plan from the anterior side 216. The anterior side 216 and the posterior side 218 may cooperatively form the main tubular body 206. The first and second limbs 212, 214 are positioned circumferentially centered with the anterior and posterior sides 216, 218 and opposite each other.

FIG. 7 shows the prosthesis 10 inserted into the existing prosthesis 200. The pivotable fenestrations 44 of the prosthesis 10 are positioned to align with the renal arteries 50 and therefore the proximal end 12 of the tubular main body 18 of the prosthesis 10 extends beyond the proximal end 208 of the main tubular body 206 of the existing prosthesis 200. The external distal leg 22 and the fenestration 24 of the prosthesis 10 are offset from the first and second limbs 212, 214 of the existing prosthesis 200. Specifically, since the external distal leg 22 of the prosthesis 10 is positioned along the anterior point 58 of the prosthesis 10, and the first limb 212 is positioned circumferentially centered between the anterior and posterior sides 216, 218 of the existing prosthesis 200, the external distal leg 22 of the prosthesis 10 must be shifted to be inserted into the first limb 212. Thus, to insert the external distal leg 22 into the first limb 212 of the existing prosthesis 200, the external distal leg 22 is moved to be positioned at an angle from the anterior point 58 of the prosthesis 10, as shown in FIG. 7.

FIG. 8 shows an iliac limb extension 220 that is inserted into the second limb 214 of the existing prosthesis 200 and then through the fenestration 24 and the internal limb 26 of the prosthesis 10. The iliac limb extension 220 includes a tubular stent graft body. The fenestration 24 and the internal limb 26 of the prosthesis 10 are offset from the second limb 214 of the existing prosthesis 200. Specifically, since the fenestration 24 and the internal limb 26 of the prosthesis 10 are circumferentially centered on the posterior side 60 of the prosthesis 10, and the second limb 214 is positioned circumferentially centered between the anterior and posterior sides 216, 218 of the existing prosthesis 200, the iliac limb extension 220 is rotated to be inserted into the fenestration 24 and the internal limb 26. In other words, the iliac limb extension 220 extends through the second limb 214 and is rotated toward the posterior side 60 of the prosthesis 10 to extend through the fenestration 24 and the internal limb 26 of the prosthesis 10. The prosthesis 10 and the iliac limb extension 220 repair the existing prosthesis 200.

It will be appreciated by those skilled in the art that changes could be made to the embodiments described above without departing from the broad inventive concept therefore. It is understood, therefore, that this invention is not limited to the particular embodiments disclosed, but it is intended to cover modifications within the spirit and scope of the present invention as defined by the claims.

The invention claimed is:

1. A bifurcated endovascular prosthesis comprising:
    a tubular main body having a diameter, a proximal end, a distal end, an internal lumen extending from the proximal end to the distal end, an anterior side, and a posterior side, the anterior and posterior sides being opposite each other circumferentially around the internal lumen;

a first limb extending from the distal end of the tubular main body along the anterior side of the main body, the first limb having a diameter less than the diameter of the tubular main body, the first limb having a proximal end and a distal end;

a first fenestration adjacent to the proximal end of the first limb, the first fenestration extending from the proximal end of the first limb to the posterior side of the tubular main body;

a second limb extending within the internal lumen from the fenestration toward the proximal end of the tubular main body;

second and third fenestrations positioned between the anterior and posterior sides of the tubular main body and circumferentially spaced from the second limb; and a fourth fenestration positioned on the anterior side of the main body and proximal to the first and second fenestrations;

wherein the first fenestration has a substantially diamond shape and a nonlinear profile; and wherein the second limb extends into the lumen along the posterior side of the tubular main body.

2. The prosthesis of claim 1, wherein the second and third fenestrations each comprises a pivotable fenestration positioned between the anterior and posterior sides of the tubular main body.

3. The prosthesis of claim 1, wherein the second and third fenestrations are spaced circumferentially opposite each other, and the first fenestration and the first limb are positioned circumferentially between the second and third fenestrations.

4. The prosthesis of claim 1, wherein the prosthesis further comprises a scallop positioned on the anterior side of the tubular main body and adjacent to the proximal end of the tubular main body.

5. The prosthesis of claim 1, wherein the first limb is circumferentially centered on the anterior side of the tubular main body.

6. The prosthesis of claim 1, wherein the first fenestration is circumferentially centered on the posterior side of the tubular main body and circumferentially opposite the fourth fenestration.

7. The prosthesis of claim 1, wherein the tubular main body and the first limb comprise a plurality of stents.

8. The bifurcated endovascular prosthesis of claim 1, wherein none of the second, third and fourth fenestrations is longitudinally aligned with the second limb.

9. A bifurcated endovascular prosthesis comprising:
a tubular main body having a diameter, a proximal end, a distal end, an internal lumen extending from the proximal end to the distal end, an anterior side, and a posterior side, the anterior and posterior sides being opposite each other circumferentially around the internal lumen;

a first limb extending from the distal end of the tubular main body along the anterior side of the main body and circumferentially centered on the anterior side of the main body, the first limb having a tubular body, a proximal end and a distal end;

a first fenestration adjacent to the proximal end of the first limb, the first fenestration extending from the proximal end of the first limb to the posterior side of the tubular main body;

a second limb extending within the internal lumen from the first fenestration toward the proximal end of the tubular main body;

second and third fenestrations positioned between the anterior and posterior sides of the tubular main body and circumferentially offset from the first fenestration and the second limb; and a fourth fenestration positioned on the anterior side of the tubular main body proximal to the second and third fenestrations and circumferentially opposite the first fenestration and the second limb;

wherein the first fenestration has a substantially diamond shape and a nonlinear profile; and wherein the second limb extends into the lumen along the posterior side of the tubular main body and is circumferentially centered on the posterior side of the tubular main body.

10. The prosthesis of claim 9, wherein the second and third fenestrations each are a pivotable fenestration positioned between the anterior and posterior sides of the tubular main body.

11. The prosthesis of claim 9, wherein the second and third fenestrations are circumferentially opposite each other.

12. The prosthesis of claim 9, wherein the prosthesis further comprises a scallop positioned on the anterior side of the tubular main body and adjacent to the proximal end of the tubular main body.

13. The prosthesis of claim 9, wherein a diameter of the first limb is smaller than the diameter of the tubular main body of the prosthesis.

14. The prosthesis of claim 9, wherein the tubular main body and the first limb comprise a plurality of stents.

15. The bifurcated endovascular prosthesis of claim 9, wherein none of the second, third and fourth fenestrations is longitudinally aligned with the second limb.

16. A bifurcated endovascular prosthesis comprising:
a tubular main body having a diameter, a proximal end, a distal end, an internal lumen extending from the proximal end to the distal end, an anterior side, an anterior point circumferentially centered on the anterior side, a posterior side, a posterior point circumferentially centered on the posterior side and circumferentially opposite the anterior point;

a first limb extending from the distal end of the tubular main body along the anterior side of the main body, the first limb having a diameter less than the diameter of the tubular main body, the first limb having a proximal end and a distal end;

a first fenestration adjacent to the proximal end of the first limb, the first fenestration extending from the proximal end of the first limb to the posterior side of the tubular main body and circumferentially opposite the anterior point;

a second limb extending within the internal lumen from the first fenestration toward the proximal end of the tubular main body;

second and third fenestrations positioned between the anterior and posterior sides of the tubular main body, wherein each of the second and third fenestrations are circumferentially offset from each other and from the first fenestration and spaced a predetermined distance from the anterior point, wherein the predetermined distance of the second fenestration to the anterior point and the predetermined distance of the third fenestration from the anterior point are substantially equal; and wherein the second limb extends into the lumen along the posterior side of the tubular main body and circumferentially opposite the anterior point.

17. The bifurcated endovascular prosthesis of claim 16, further comprising a fourth fenestration positioned on the anterior side at the anterior point of the tubular main body proximal to the second and third fenestrations and circumferentially offset from the second and third fenestration and circumferentially opposite the first fenestration and posterior point.

18. The bifurcated endovascular prosthesis of claim 17, wherein the second and third fenestrations are approximately 90 degrees from the anterior point.

19. The bifurcated endovascular prosthesis of claim 16, wherein the first fenestration has a substantially diamond shape and a nonlinear profile.

20. The bifurcated endovascular prosthesis of claim 16, wherein neither of the second and third fenestrations is longitudinally aligned with the second limb.

21. A bifurcated endovascular prosthesis comprising:
   a tubular main body having a diameter, a proximal end, a distal end, an internal lumen extending from the proximal end to the distal end, an anterior side, an anterior point circumferentially centered on the anterior side, a posterior side, a posterior point circumferentially centered on the posterior side and circumferentially opposite the anterior point;
   a first limb extending from the distal end of the tubular main body along the anterior side of the main body, the first limb having a diameter less than the diameter of the tubular main body, the first limb having a proximal end and a distal end;
   a first fenestration adjacent to the proximal end of the first limb, the first fenestration extending from the proximal end of the first limb to the posterior side of the tubular main body circumferentially opposite the anterior point;
   a second limb extending within the internal lumen from the first fenestration toward the proximal end of the tubular main body along the posterior side of the tubular main and circumferentially opposite the anterior point;
   a plurality of second fenestrations that are circumferentially offset from each other, the first fenestration, the second limb, and the posterior point such that none of the plurality of second fenestrations is longitudinally aligned with the second limb.

* * * * *